United States Patent [19]

Nishikawa et al.

[11] 4,365,340
[45] Dec. 21, 1982

[54] DENTAL RADIOGRAPHIC APPARATUS FOR PHOTOGRAPHING ENTIRE JAWS AND TAKING CEPHALOGRAM

[75] Inventors: Kazuo Nishikawa, Yawata; Kazuo Hozumi, Ohtsu, both of Japan

[73] Assignee: Kabushiki Kaisha Morita Seisakusho, Kyoto, Japan

[21] Appl. No.: 274,228

[22] Filed: Jun. 16, 1981

[30] Foreign Application Priority Data

Jun. 20, 1980 [JP] Japan .................................. 55/087466

[51] Int. Cl.³ .............................................. A61B 6/14
[52] U.S. Cl. ..................................... 378/039; 378/197
[58] Field of Search ............................ 378/39, 197, 40

[56] References Cited

U.S. PATENT DOCUMENTS 4,242,585 12/1980 Yamano ............................. 378/39

Primary Examiner—Alfred E. Smith
Assistant Examiner—T. N. Grigsby
Attorney, Agent, or Firm—Koda and Androlia

[57] ABSTRACT

This disclosure relates to an X-ray photographing apparatus both for photographing the entire jaws and for cephalographic use. The apparatus is constructed in such a manner that, in setting the generator in any direction either for cephalographic use or for use in photographing the entire jaws, the X-ray generator is automatically vertically rotated through a specified angle and is enabled to make simple and correct change in the direction of irradiation by providing the X-ray generator mounted horizontally and vertically rotatably at one end of a rotary arm with a sliding element, providing the arm with an inclined guide groove for guiding the element therein, and merely rotating the generator horizontally through a specified angle.

4 Claims, 6 Drawing Figures

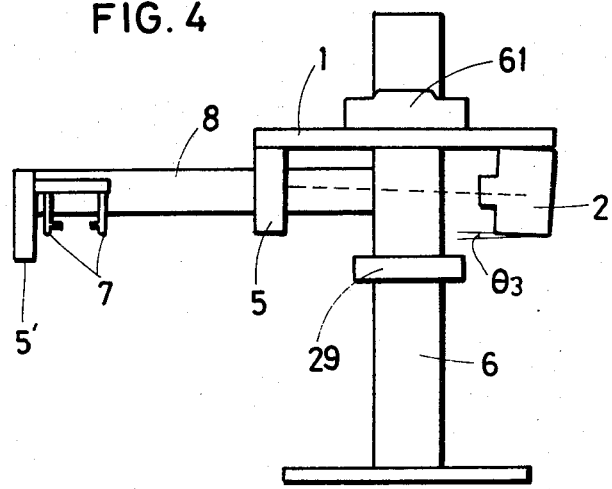
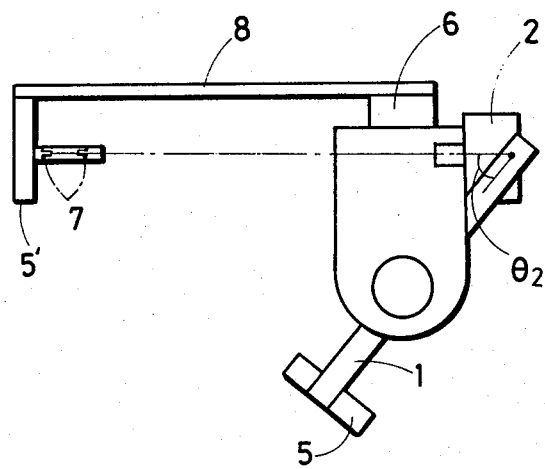

DENTAL RADIOGRAPHIC APPARATUS FOR PHOTOGRAPHING ENTIRE JAWS AND TAKING CEPHALOGRAM

BACKGROUND OF THE INVENTION

1. Field of the Invention

This invention relates to a radiographic apparatus for use in photographing the entire jaws concurrently capable of taking a cephalogram, and more particularly to a radiographic apparatus for photographing the entire jaws designed to control an angle of an X-ray generator and to manipulate setting of the angle with great ease.

2. Prior Art

The radiographic apparatus for use in photographing the entire jaws and concurrently capable of taking a cephalogram which has heretofore been used comprises, as typically shown in FIG. 4, a stanchion 6 having a fixed arm 8 projecting on one side, a rotary arm 1 mounted horizontally rotatably on a support projecting forwardly from the stanchion 6, an X-ray generator 2 mounted horizontally and vertically rotatably at one end of the rotary arm 1, a film cassette 5 for photographing the entire jaws mounted at the other end of the arm 1, a cephalographic radiographic film cassette 5' mounted at the tip of the fixed arm 8, and a pair of ear rods 7 adjacent to the cassette 5'. When an operator takes an X-ray photograph of the entire jaws by the use of the conventional radiographic apparatus of the type described, the operator sets the X-ray generator 2 by inclining the generator 2 upwardly at an angle of $\theta_3$ (generally 5-8 degrees) along the direction of axis shaft-line of the rotary arm 1 and photographs while rotating the arm 1 so that the X-ray generator 2 may be brought into an opposed relation with respect to the film cassette 5 on the opposite of the generator 2. On the other hand, when it is desired to take an X-ray cephalogram, the operator makes the X-ray picture by placing the X-ray generator 2 on the straight line connecting a pair of ear rods 7 to each other as shown in FIG. 5 and rotating the generator 2 horizontally through a specified angle $\theta_2$, rotating the same vertically through an angle of $\theta_3$ to make the same horizontally, and setting the generator 2 so that the same may be brought into an opposed relation with respect to the film cassette 5' at the top of the fixed arm 8.

However, in the apparatus above, as shown in FIG. 6, the X-ray generator 2 is mounted horizontally and vertically rotatably at one end of the rotary arm 1 in such a manner that the generator 2 is permitted to be rotated horizontally by providing an inverted U-shaped hand 10 horizontally rotatably at the lower end of a vertically fixed shaft 9 at the tip of the rotary arm 1 and pivotally connecting the X-ray generator 2 to the hand 10. Accordingly, when it is desired to change the state of the apparatus set for photographing the entire jaws shown in FIG. 6 to cephalographic use, it is first necessary to raise a horizontal positioning pin 11, rotate the X-ray generator 2 together with the inverted U-shaped hand 10 clockwise, insert the pin 11 into the next hole 12 and rotate the direction of the generator 2 horizontally through a specified angle $\theta_2$. Thereafter, all that is necessary is to raise a vertical positioning pin 13, rotate the generator 2 vertically through an angle $\theta_3$, insert the pin 13 into the next hole 14 to make the generator 2 horizontal and to bring the same into an opposed position with respect to an X-ray film cassette 5' for cephalographic use. In this manner, the conventional type apparatus was of the construction which made it necessary to control the two specified angles separately with respect to a horizontal and vertical direction, resulting in great inconvenience to users.

SUMMARY OF THE INVENTION

An object of the invention is to provide a radiographic apparatus for use in photographing the entire jaws and concurrently capable of taking a cephalogram, which apparatus is capable of simply and correctly setting the X-ray generator so that the generator may be automatically rotated vertically through a specified angle by merely rotating the X-ray generator horizontally through a specified angle even when the generator is set for cephalographic use or for use in photographing the entire jaws.

The object of the invention described above can be achieved by providing an X-ray generator vertically and horizontally rotatably mounted on a rotary arm with a sliding element and providing the rotary arm with a guide groove having a specified angle of inclination for guiding the sliding element to cause the generator to make vertical rotation to thereby control an angle of vertical rotation when the control is made of horizontal rotation of the X-ray generator.

A detailed description will now be given of a preferred embodiment of the invention with reference to the accompanying drawings.

BRIEF DESCRIPTION OF THE DRAWINGS

FIG. 4 is a front elevation view of the conventional type apparatus;

FIG. 5 is a plan view of the conventional type apparatus; and

DETAILED DESCRIPTION OF THE INVENTION

Figure 1:
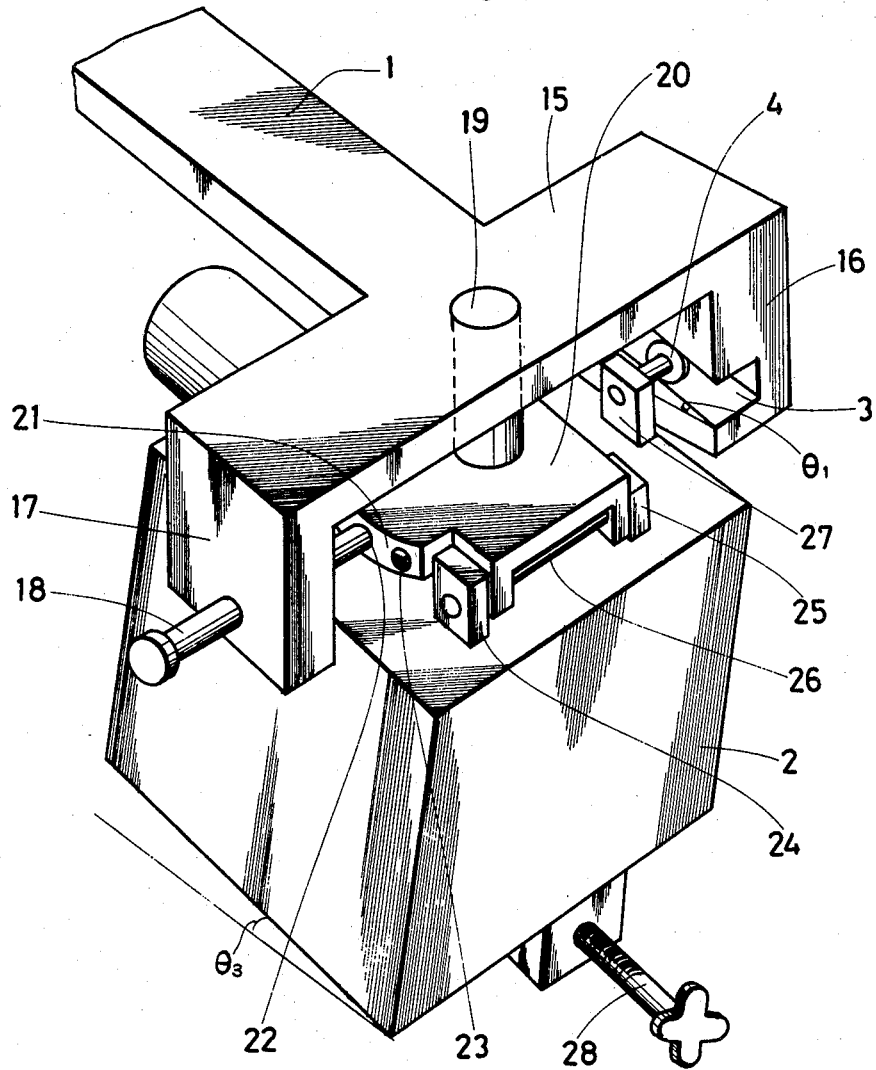
FIG. 1 is a perspective view of the essential part of a preferred embodiment of the invention showing the state of an X-ray generator set for photographing the entire jaws.

The radiographic apparatus for use both in photographing the entire jaws and in taking a cephalogram provided by the invention is the same in general structure as the conventional apparatus in FIG. 4. The apparatus of the invention comprises a stanchion 6 having a fixed arm 8, a rotary arm 1 horizontally rotatably mounted on a support projecting forwardly of the stanchion 6, an X-ray generator 2 horizontally and vertically rotatably mounted at one end of the rotary arm 1, a film cassette 5 for photographing the entire jaws mounted at the other end of the arm 1, a film cassette 5' for cephalographic use mounted at the tip of the fixed arm 8, and a pair of ear rods 7 adjacent to the film cassette 5 .

Figure 2:
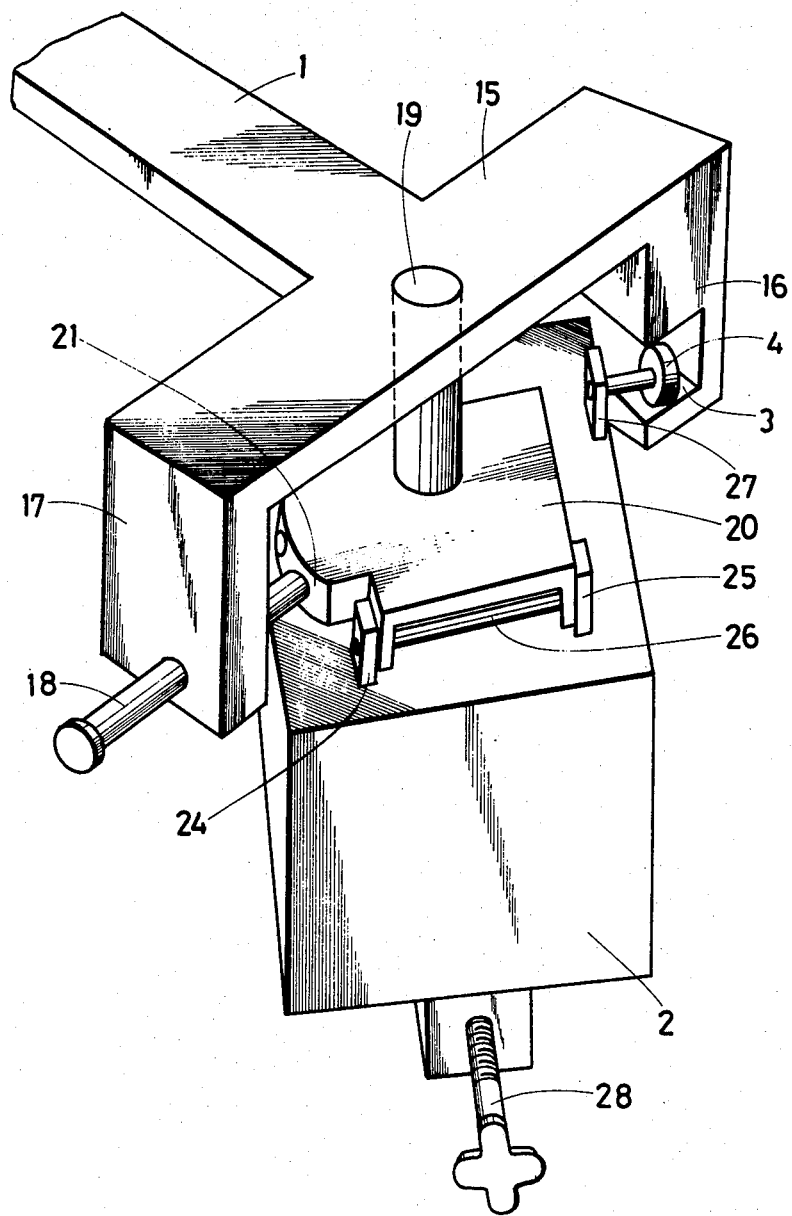
FIG. 2 is a perspective view of another embodiment similar to FIG. 1 but showing the state of the generator set for cephalographic use.

The main characteristic of the invention lies in the mounting portion of the X-ray generator 2 with respect to the rotary arm 1. In FIGS. 1 and 2, the rotary arm 1 is formed at its end with an inverted U-shaped hand 15.

The hand 15 is formed on the inside surface of one depending side piece 16 with a groove 3, and is formed on the other depending side piece 17 with a positioning pin 18 which is used as a means for fixing the X-ray generator 2 and which passes transversely through the side piece 17. The guide groove 3 is formed so as to have a specified angle of inclination $\theta_1$, which will be presently described.

To the center of the U-shaped hand 15 is fixed a vertically fixed shaft 19 extending downwardly and a horizontal rotary plate 20 is horizontally rotatably mounted at the lower end of the fixed shaft 19. The side surface of the horizontal rotary plate 20 facing the positioning pin 18 is formed with an arcuate side 21. The arcuate side 21 is formed with a space of angle corresponding to the angle of horizontal rotation $\theta_2$ required when the state of the generator 2 set for X-ray photographing of the entire jaws is to be changed to the state of the generator set for cephalographic use, and the arcuate side 21 is further provided with side holes 22 and 23. The side holes 22 and 23 are adapted to receive the tip of the pin 18 thereinto.

The X-ray generator 2 is provided with a pair of projections 24 and 25 formed on the upper wall of the generator, and the projections 24 and 25 support the horizontal rotary plate 20 by a shaft 26 journaled vertically rotatably in the end of the plate 20. At one end of the upper wall of the generator 2 adjacent to the aforementioned guide groove 3 is formed a vertical projection 27 to which a roller 4 in the form of a sliding element which is slidable along the inside of the groove 3 is rotatably journaled. Accordingly, the vertical rotation of the generator 2 is controlled by the engagement of the roller 4 with the groove 3.

Figure 3:
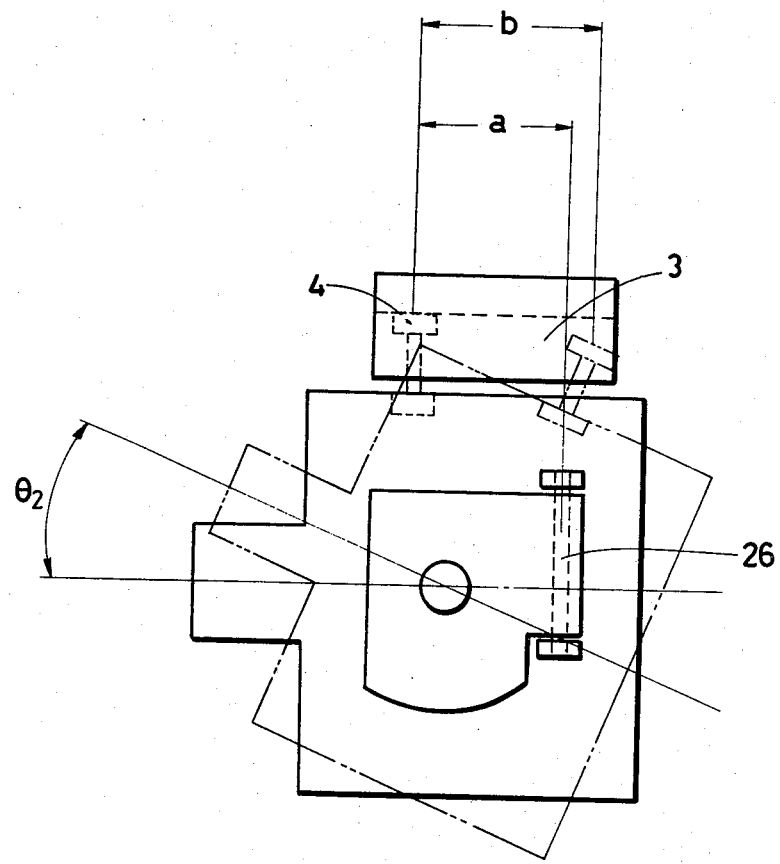
FIG. 3 is an explanatory diagram illustrating the operation of the essential part of the embodiment of FIG. 1.
Figure 6:
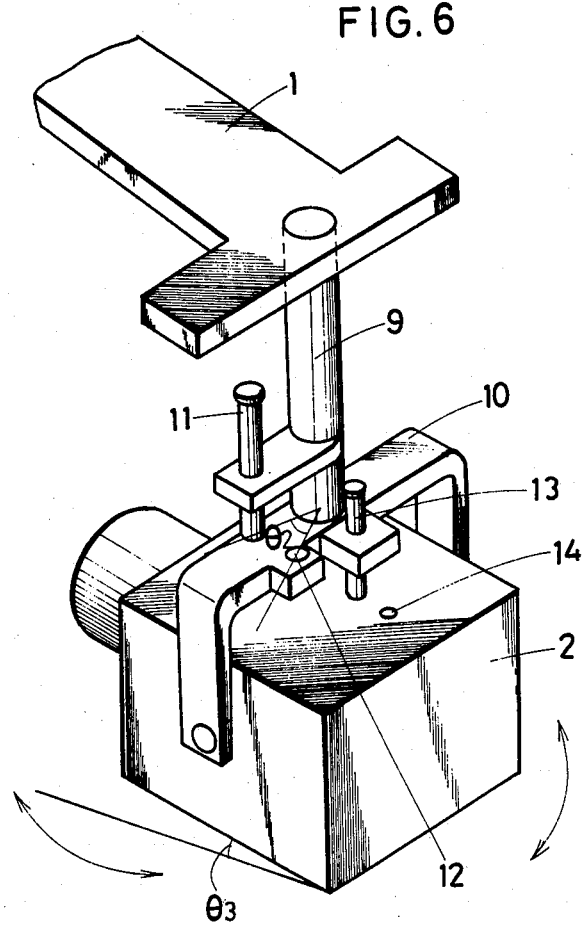
FIG. 6 is a perspective view of the essential part of the conventional type apparatus.

The guide groove 3 is formed at an angle of inclination $\theta_1$ as previously described, the angle is set in the following manner. Namely, as shown in FIG. 3, if the horizontal distance between the shaft 26 and the shaft of the roller 4 is set as a, and a distance over which the roller 4 shifts horizontally in the direction of the groove 3 when the generator 2 is clockwise rotated horizontally through an angle $\theta_2$ from the solid line state for photographing the entire jaws to the two-dotted chain lines state for cephalographic use is set as b, and an angle of inclination of the generator 2 in the state of the generator 2 for photographing the entire jaws is set as $\theta_3$, then an angle of inclination $\theta_1$ of the guide groove 3 is formed by the equation:

$$\tan(\theta_1) = (a/b) \cdot \tan(\theta_3)$$

The guide groove 3 in the embodiment illustrated is shown as a linear groove, but it should be understood that the groove 3 may be formed arcuate along the arcuate locus of the roller 4 rolling inside the groove. Also, the embodiment is constructed such that the generator 2, in the cephalographic use, may invariably rotate clockwise for taking a cephalogram so as to bring the generator 2 also into use for a radiograph of the type in which, as shown in FIG. 4, the fixed arm 8 having a film cassette 5' for cephalographic use at the tip of the arm 8 is provided so as to project on the lefthand side of the stanchion 6. However, when the radiographic apparatus is of the type in which the fixed arm 8 projects to righthand side of the stanchion 6, it is only necessary that the guide 3 be formed oppositely inclined to make the generator 2 turn counterclockwise.

In the drawings, the numeral 28 designates a set screw provided on the backside of the generator 2, and the screw 28 is intended to firmly fix the generator 2 by being screwed into a screw hole of the side surface of the horizontal plate 29 of the stanchion 6 in the state of the generator 2 being set for cephalographic use.

As described above, according to the invention, when it is desired to change the generator 2 from the state of the generator being set for photographing the entire jaws in FIG. 1 to the state of the generator 2 being set for cephalographic use in FIG. 2, all that is necessary is to position the generator 2 on the line connecting to a pair of ear rods 6 by rotating the arm 1 and to rotate the generator 2 horizontally through an angle $\theta_2$ with keeping the positioning pin 18 pulled out and then to insert the pin 18 into the next hole 23. In this manner, mere horizontal rotation of the generator 2 causes the roller 4 of the generator 2 to roll inside the guide groove 3, resulting the automatic vertical control of rotation of an angle $\theta_3$ of the generator 2, which, in turn, causes the generator 2 to face the direction of irradiation in cephalographic use. Similarly, when it is desired to return the generator 2 to the position in which the generator 2 is used for photographing the entire jaws, mere horizontal rotation of the generator 2 in the opposite direction makes it possible to provide the direction of irradiation in which the generator is given a specified angle of inclination $\theta_3$. Accordingly, the apparatus of the invention is greatly convenient, because the angle setting manipulation is reduced by half in comparison with the conventional apparatus.

We claim:

1. A radiographic apparatus having an X-ray generator horizontally and vertically rotatably mounted at one end of a rotary arm and designed to set the generator in any direction of irradiation either for cephalographic use or for use in photographing the entire jaws, said apparatus being characterized in that said generator is provided with a sliding element and a guide groove for said sliding element in said rotary arm, said groove being inclined to guide said sliding element to make automatic vertical rotation of said X-ray generator through a specified angle for changing the direction of the generator from one state of the generator set either for cephalographic use or for use in photographing the entire jaws to the other state thereof set for photographing.

2. An apparatus according to claim 1, wherein said sliding element is a roller rolling inside said guide groove.

3. An apparatus according to claim 1, wherein one end of said rotary arm is formed into an inverted U-shaped hand, said hand being provided on the inside surface of one depending side piece with an inclined guide groove, said groove being provided with a sliding element fitted into said groove projecting at a position adjacent to the guide groove at the upper end of said generator.

4. An apparatus according to claim 3, wherein said generator is mounted vertically rotatably on a horizontal rotary plate horizontally fixed to a vertically fixed shaft provided at the center of said inverted U-shaped hand, said shaft extending downward and a positioning pin inserted into the other depending side piece of the inverted U-shaped hand is designed to be inserted into either one of two side holes formed on the arcuate side of said horizontal rotary plate with a space from each other so as to permit a specified angle of horizontal rotation.

* * * * *